(12) United States Patent
Vitagliano et al.

(10) Patent No.: US 8,461,110 B2
(45) Date of Patent: Jun. 11, 2013

(54) HETERODIMERIC PEPTIDE COMPOUNDS DISPLAYING NGF ACTIVITY AND THEIR USE TO TREAT NEURODEGENERATIVE DISORDERS

(75) Inventors: Luigi Vitagliano, Naples (IT); Laura Zaccaro, Naples (IT); Giancarlo Morelli, Naples (IT); Enzo Martegani, Vignate (IT)

(73) Assignee: Blueprint Pharma S.R.L., Milan (IT)

( * ) Notice: Subject to any disclaimer, the term of this patent is extended or adjusted under 35 U.S.C. 154(b) by 940 days.

(21) Appl. No.: 11/922,043

(22) PCT Filed: Jun. 9, 2006

(86) PCT No.: PCT/EP2006/005522
§ 371 (c)(1),
(2), (4) Date: Sep. 11, 2009

(87) PCT Pub. No.: WO2006/133853
PCT Pub. Date: Dec. 21, 2006

(65) Prior Publication Data
US 2009/0318335 A1  Dec. 24, 2009

(30) Foreign Application Priority Data
Jun. 13, 2005  (EP) .................... 05012643

(51) Int. Cl.
*A61K 38/18* (2006.01)
*C07K 14/48* (2006.01)

(52) U.S. Cl.
USPC ............ 514/8.4; 530/300; 530/317; 530/324; 930/120; 930/260

(58) Field of Classification Search
None
See application file for complete search history.

(56) References Cited

U.S. PATENT DOCUMENTS
5,958,875 A   9/1999 Longo et al. ............... 514/11
6,017,878 A * 1/2000 Saragovi et al. ............ 514/8.4

OTHER PUBLICATIONS

Xie et al. Nerve Growth Factor (NGF) Loop 4 Dimeric mimetics . . . The Journal of Biological Chemistry. Sep. 22, 2000, vol. 75, No. 38, pp. 29868-29874.*
Saragovi et al., "Small Molecule Peptidomimetic Ligands of Neurotrophin Receptors, Identifying Binding Sites, Activation Sites and Regulatory Sites", Current Pharmaceutical Design 8(24):2201-2216 (2002).
LeSauteur et al., "Small Peptide Mimics of Nerve Growth Factor Bind TrkA Receptors and Affect Biological Responses", J Biol Chem 270(12):6564-6569 (1995).
Beglova et al., "Design and Solution Structure of Functional Peptide Mimetics of Nerve Growth Factor," J Med Chem 43:3530-3540 (2000).

* cited by examiner

*Primary Examiner* — Jeffrey E Russel
(74) *Attorney, Agent, or Firm* — Fish & Richardson P.C.

(57) ABSTRACT

Peptides having a structure characterized by the presence of two loops constrained in cyclic structure by the presence of covalent bonds between amino acid side chains, the amino acid sequences of the first and the second loop being substantially homologues to that of loop 1 (residues 29-38) and of loop 4 (residues 92-97) of NGF, respectively, displaying nerve growth factor (NGF) agonist or partial agonist activity.

21 Claims, 3 Drawing Sheets

L1L4

Loop1  Loop4

(SEQ ID NO: 4)

AcNL1L4

Loop1  Loop4

(SEQ ID NO: 5)

HETERODIMERIC PEPTIDE COMPOUNDS DISPLAYING NGF ACTIVITY AND THEIR USE TO TREAT NEURODEGENERATIVE DISORDERS

SUMMARY OF THE INVENTION

The invention relates to new peptides having a structure characterized by the presence of two loops, with unrelated amino acid sequences, constrained in cyclic structure by the presence of covalent bonds between amino acid side chains. The amino acid sequence of the first loop is substantially homologous to that of loop 1 (residues 29-38) of Nerve Growth Factor (NGF) whereas the second is substantially homologous to loop 4 (residues 92-97) of NGF. The peptides mimic the NGF activity through specific interaction with NGF receptors. The NGF activity displayed by the peptides of the invention, containing two different loops in the sequence, results much higher than that displayed by peptides having a single loop structure or having a structure characterized by two loops with identical or related sequences.

The invention also concerns multimeric compounds in which two molecules of the type described above, are covalently bound to form multimers, which are able to establish interactions with the two subunits of the trkA dimer.

The invention also concerns the preparation of the pharmaceutical compositions for the treatment of diseases involving NGF-responsive cells.

BACKGROUND OF THE INVENTION

Nerve growth factor (NGF) is the best known member of the neurotrophin family of growth factors (M. Bothwell. (1995) Annu Rev Neurosci., 18, 223-53). In its active form, NGF is a dimeric protein, composed by two identical polypeptide chains, that can bind two different cellular receptors trkA and p75 (C. Wiesmann, A. M. de Vos. (2001) Cell Mol Life Sci.; 58, 748-59; X. L. He, K. C. Garcia. (2004) Science. 7, 870-5.). Interestingly, the activation of these receptors produces divergent results. Indeed, activation of trkA provides protection against apoptotic cell death, whereas p75 mediates apoptosis in some neuronal cells. trkA is a transmembrane tyrosine kinase receptor that transduces NGF signals. As found for other receptors of the tyrosine kinase family, the dimeric NGF protein induces trkA dimerization, which leads to the auto-phosphorylation of the receptor and to the activation of essential cellular pathways.

NGF regulates neuronal survival, promote neurite outgrowth, and up-regulates certain neuronal functions such as mediation of pain and inflammation. NGF is also important for the regulation of neurons during development and in neuron regeneration after injury. In principle NGF could be used in the treatment of several pathological states. Target diseases include neuropathies of NGF-dependent neurons, therapy of acute nervous system injury such as ischemic stroke and spinal cord injury, and neuroectoderm-derived tumors. However, several limitations preclude the use of proteins as therapeutic agents (H. U. Saragovi, M. C. Zaccaro. (2002) Curr Pharm Des. 8, 2201-16). These include (a) the high level of proteolytic degradation of proteins, (b) difficulties associated with their administration limit, (c) their restricted penetration of the central nervous system, and (d) their availability in limited amounts. Therefore, it is desirable to search for new neurotrophic factor mimetics to overcome the drawbacks related to the use of NGF. Several different approaches have been developed in this research area. In particular, attempts to design different classes of compounds aimed at (a) activating, directly or indirectly, Trk receptors, (b) enhancing the actions of NTs on Trk receptors, or (c) influencing NTs expression and secretion have been carried out.

Particularly attractive is the search for small molecules, peptidic or non-peptidic, that bind to selective receptors and either mimic or antagonize neurotrophin activity. Different alternative strategies have been used to achieve this scope (H. U. Saragovi, M. C. Zaccaro. (2002) Curr Pharm Des. 8, 2201-16; S. M. Massa, Y. Xie, F. M. Longo. (2003) J Mol Neurosci., 20, 323-6). These include the screening of natural products and the rational design of novel compounds. Among the natural products, the fungal non-peptide metabolite L-783,281 is able to induce trkA auto-phosphorylation (N. Wilkie, P. B. Wingrove, J. G. Bilsland, L. Young, S. J. Harper, F. Hefti, S. Ellis, S. J. Pollack S J. (2001) J Neurochem. 78, 1135-45). Although the mechanism of action of this compound is not fully elucidated, it is believed that it interacts with the intracellular portion of trkA. The rational design of trkA ligands was carried out by considering regions of the sequences of anti-trkA antibodies and of NGF. Investigations on the trkA antibody, named 5C3, have shown that it promotes receptor internalization and PI(3)K signalling (L. LeSauteur, N. K. Cheung, R. Lisbona, H. U. Saragovi. (1996) Nat Biotechnol., 14, 1120-2). However, no effect on neuronal cells has been reported. A peptidomimetic approach that integrates information derived from 5C3 with the trkA-binding properties of peptides derived NGF sequence has leaded to the identification of a novel compound denoted as D30, that binds to trkA but does not compete with NGF. This molecule also protects embryonic DRG neurons from apoptosis.

Many efforts have been made to design NGF mimetics using data available on this neurotrophin. Multiple techniques have been used to deduce which regions of the NGF protein interact with NGF receptors (H. U. Saragovi, M. C. Zaccaro. (2002) Curr Pharm Des. 8, 2201-16; S. M. Massa, Y. Xie, F. M. Longo. (2003) J Mol Neurosci., 20, 323-6). Valuable information has been derived from structural investigations on complexes between neurothrophins and Trk receptors and from mutagenesis studies (C. Wiesmann, A. M. de Vos. (2001) Cell Mol Life Sci.; 58, 748-59). Regions corresponding to the loops 1 (residues 29-35), the loop 2 (residues 40-49), the loop 4 (residues 91-97), and the N-terminus (residues 1-25) have been identified as potential candidates. However, it has been found that linear peptides derived from NGF fragments do not show any biological activity. Data on cyclic peptides based on the loop 1 sequence are somewhat unclear. These molecules apparently interact with the p75 receptors rather than trkA and act as partial NGF agonists in promoting survival but not neurite outgrowth in dorsal root ganglion neurons. Compounds with NGF agonist activity, although rather limited, have been obtained by making cyclic derivatives of the loop 4 sequence. In order to mimic the biological action of NGF, homodimeric cyclic peptides based on loop 4 have also been developed (U.S. Pat. No. 5,958,875). These compounds show an enhanced agonist activity when compared to their monomeric counterparts which corresponds approximately to 20-40% of the NGF, when used in the 40-60 nM concentration range (H. U. Saragovi, M. C. Zaccaro. (2002) Curr Pharm Des. 8, 2201-16).

However, the use of these peptides is still limited by their relatively low efficacy when compared to NGF.

DESCRIPTION OF THE INVENTION

It has now been found that, by combining, in the same molecular entity, different regions of NGF fragments containing loop 1 and loop 4, which, as individual fragments, are believed to interact with different receptors (p75 and trkA) it is possible to obtain compounds with an NGF agonist activity which is significantly enhanced when compared to single loops peptide and homodimeric peptides.

The invention relates to new peptides having a structure characterized by the presence of two loops constrained in cyclic structure by the presence of covalent bonds between amino acid side chains. The amino acid sequences of the first and the second loop of these molecules are substantially homologues to that of loop 1 (residues 29-38) and of loop 4 (residues 92-97) of NGF, respectively.

The peptides of the invention display a NGF agonist activity such as auto-phosphorylation of trkA, DRG differentiation, and survival.

The NGF activity displayed by the peptides of the invention, containing two different loops in the sequence, results much higher than that displayed by peptides having a single loop structure or having a structure characterized by two loops with identical or related sequence.

Dorsal root ganglia (DRG) were prepared from 8-days old chick embryos and cultured in the presence of peptide L1L4 (C) or AcL1L4 (D) both at final concentration of 6 μM. As a control, ganglia were treated with 2.5 S mNGF (10 ng/ml, 0.38 nM) (B) or maintained in culture medium (DMEM supplemented with 10% FBS) (A). Photographs in the figure were taken after 4 days in culture and are representative of several experiments with similar results. The same level of differentiation was obtained with a lower dose (3 μM). Treatments were repeated every three days and ganglia monitored daily for neurite processes extension under a reversed microscope equipped with an Olympus camera.

Figure 3:
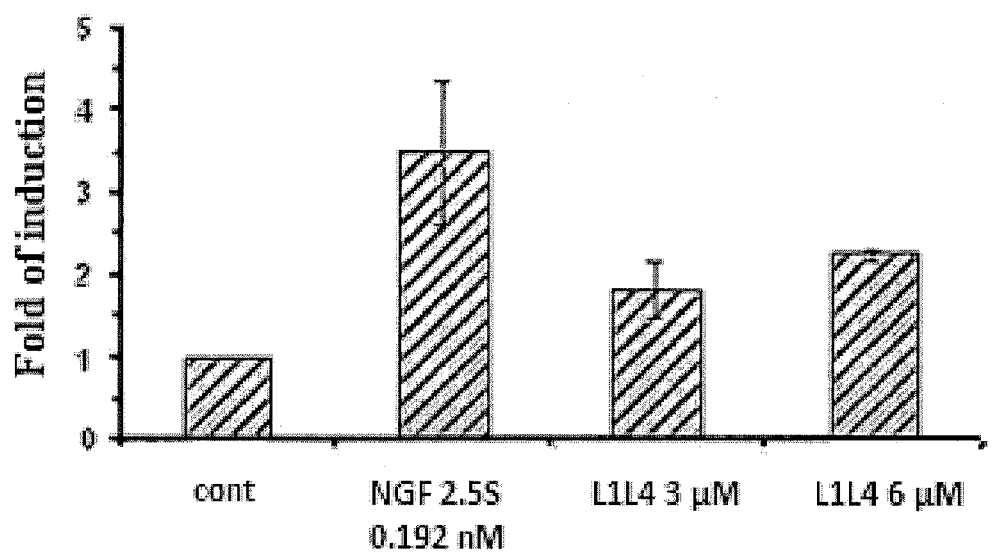

FIG. 3. Levels of trkA Phoshorylation induced by the NGF peptide L1L4

PC12 cells were exposed for 5 min to the NGF peptide L1L4 (3 or 6 μM) or to 2.5 S mNGF (5 ng/ml) and 300 μg of total proteins immunoprecipitated with anti-pan-trk Ab (C-14, Santa Cruz Biotechnology). Immunocomplexes were separated on 7.5% SDS-PAGE and p-trkA detected by probing the membrane with the anti-p-Tyr mAb (PY99, Santa Cruz Biotechnology). Quantification of the p-trkA species was performed by densitometric analysis of the bands by using Scion Image software. Data are the mean±SE of three separate experiments and are expressed as fold of induction (arbitrary units) vs. control.

DETAILED DESCRIPTION OF THE INVENTION

This invention concerns the finding and the development of new peptide or peptidomimetic compounds displaying NGF agonist or NGF partial agonist activity and their use to treat neurodegenerative disorders.

An "NGF agonist" or "NGF partial agonist" is defined as any compound capable of promoting at least one of the biological responses normally associated with NGF. For example, any compound capable of supporting at least one of the biochemical or morphological NGF responses, such as binding to the receptors, or activation of the trkA receptor (auto-phosphorylation), or neuronal survival, or neurite outgrowth, in the absence of NGF is defined as an NGF agonist.

The biological activity of the compounds object of this invention is due to interaction of the new molecules with the NGF high affinity receptor trkA.

The new peptides of the invention have a structure characterized by the presence of two loops constrained in cyclic structure by the presence of covalent bonds between amino acid side chains. The amino acid sequence of the two loops are substantially homologues to that of loop 1 (residues 29-38) and loop 4 (residues 92-97) of NGF.

The compounds of the invention may be represented by the following formula:

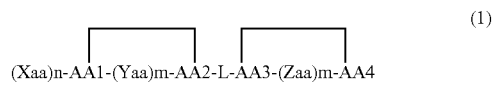

(Xaa)n-AA1-(Yaa)m-AA2-L-AA3-(Zaa)m-AA4   (1)

wherein:
AA1 and AA2 are chosen in the group of Cys, Asp, Glu, Lys, Orn, Pen or Dap and are linked through an amide or S—S bond between chemical functions on their side chains;
AA3 and AA4 are chosen in the group of Cys, Asp, Glu, Lys, Orn, Pen or Dap and are linked through an amide or S—S bond between chemical functions on their side chains;
L is a linker sequence formed by 2-4 amino acid residues, an organic linker or a mixed sequence of amino acid residues and organic linker;
(Yaa)m is an amino acid sequence formed by 4-8 residues;
(Zaa)m is an amino acid sequence formed by 4-8 residues;
(Xaa)n is an amino acid sequence in which n is an integer from 0 and 22;
L is preferably the sequence TGA. An example of a suitable organic linker is the di-oxoethylene group.
(Yaa)m is preferably a sequence homologue to that of loop 1 (residues 29-38) of NGF, the sequence TDIKGK (SEQ ID NO:1) being particularly preferred.
(Zaa)m is preferably a sequence homologue to that of loop 4 (residues 92-97) of NGF. The sequence DGKQ (SEQ ID NO:2) is particularly preferred.
When n is not zero, (Xaa)n preferably represents a sequence homologue to that of N-terminus of NGF, in particular the sequence HPIFHRGEFSVADSVSVWVGD (SEQ ID NO:3). HPIFHRGEFSVADSVSVWVGD.

The peptides of the invention could be amine free or acetylated on the N-terminus, they could be in carboxylic free form or as amide in the C-terminal position; one or two more amino acid residues could be added on the C-terminal end.

The position of the first and the second loop along the polypeptide chain can also be reversed.

The peptide of the invention could also be a dimeric form of peptides of formula (1). In this case, a covalent bond is present between the monomeric peptides.

For the compounds of the invention which contain amino acids, the amino acid residues are denoted by single-letter or three-letter designations following conventional practices. All of the amino acids used in the present invention may be either the D- or L-isomer. The L-isomers are preferred when not otherwise specified. Commonly encountered amino acids which are not gene-coded may also be used in the present invention. These amino acids and their abbreviations include ornithine (Orn); aminoisobutyric acid (Aib); benzothiophenylalanine (BtPhe); albizziin (Abz); t-butylglycine (Tle); phenylglycine (PhG); cyclohexylalanine (Cha); norleucine (Nle); 2-naphthylalanine (2-Nal); 1-naphthylalanine (1-Nal); 2-thienylalanine (2-Thi); 1,2,3,4-tetrahydroisoquinoline-3-carboxylic acid (Tic); N-methylisoleucine (N-MeIle);

homoarginine (Har); N.-alpha.-methylarginine (N-MeArg); phosphotyrosine (pTyr or pY); pipecolinic acid (Pip); 4-chlorophenylalanine (4-C1Phe); 4-fluorophenylalanine (4-FPhe); 1-aminocyclopropanecarboxylic acid (1-NCPC); and sarcosine (Sar). The term "substantially homologous" means that the amino acid sequence of a particular compound bears a substantial correspondence to the amino acid sequence of native murine or human NGF or other members of the neurotrophin family. Exemplary members of the neurotrophin family are NGF, BDNF, NT-3 and NT-4/5. Typically, the residues of an amino acid sequence of the particular compound will be at least about 50%, preferably at least about 75%, more preferably at least about 90% homologous to the residues of the amino acid sequence of native NGF. Alternatively, at least about 50%, preferably at least about 75%, more preferably at least about 90% of the amino acid sequence will be composed of residues which are biologically functional equivalents of the corresponding residues in NGF.

When it is mentioned that the amino acid sequence of the peptide fragment should be substantially homologues to the sequence of the native NGF, the parent amino acid should be substituted by biologically functional equivalent residues. Biologically functional equivalent substitutes for a parent amino acid may be another amino acid or amino acid analogue which is in the same class as the parent amino acid. For example, the nonpolar (hydrophobic) amino acids include alanine, leucine, isoleucine, norleucine, valine, norvaline, proline, phenylalanine, tyrosine, tryptophan, cysteine and methionine, methionine oxide and methionine dioxide. Amino acids with aromatic side chains include histidine, phenylalanine, tyrosine and tryptophan. The polar neutral amino acids include glycine, serine, homoserine (Hse), threonine, cysteine, tyrosine, asparagine and glutamine. The positively charged amino acids include arginine, homoarginine, ornithine, histidine and lysine. The negatively charged amino acids include aspartic acid and glutamic acid.

The peptide or peptidomimetic molecules of the present invention can be synthesized in a manner similar to methods conventionally used in ordinary peptide chemistry. Such known methods are described in, for example, M. Bodansky and M. A. Ondetti, Peptide Synthesis, published by Interscience Publishing Co., New York, 1966; F. M. Finn and K. Hofmann, The Proteins, volume 2, edited by H. Neurath, R. L. Hill, Academic Press Inc., New York, 1976; Nobuo Izumiya et al., Peptide Synthesis, published by Maruzen Co., 1976; Nobuo Izumiya et al., Fundamental Peptide Synthesis and Experiment, published by Maruzen Co., 1985; Lecture Series on Biochemical Experiment, edited by the Association of Biochemistry, Japan, volume 1, "Chemistry of Protein IV", chapter II, Haruaki Yajima, Peptide Synthesis, 1977. The peptide can be synthesized by selecting the liquid phase method or the solid phase method, depending on the structure of the peptide. The peptides could also be synthesized by combining the solution and the solid phase methods.

Another relevant aspect of this invention relates to compounds having sequences of amino acid residues or biological functional equivalents thereof, the sequence being substantially homologous to residues 29-38 of NGF (loop 1), and residues 92-97 of NGF (loop 4), wherein a fragment of the sequence of amino acids is in a conformationally constrained structure such as a ring. Such constrained structures can be derived by several methods including, but not limited to: (1) Cyclizing via the formation of a bond between the side chains of two residues, e.g., by forming a amide bond between an aspartate or glutamate side chain and a lysine side chain, or by disulfide bond formation between two cysteine side chains or between a penicillamine and cysteine side chain or between two penicillamine side chains, (2) Cyclizing via the formation of an amide bond between a side chain (e.g., lysine or ornithine) and the C-terminal carboxyl respectively, (3) Linking two side chains with a short carbon spacer group.

Many synthetic strategies are available to obtain the simultaneously presence of two loops in the same molecule. For example, the covalent bond could be obtained in solid phase during the assembly of the peptide, or could be obtained in solution after selective deprotection of corresponding amino acids. Orthogonal protecting side-chain groups should be used in order to obtain selective cyclization.

The peptides of the invention can be purified by reverse-phase high pressure liquid chromatography and characterised by mass spectrometry, amino acid analysis, NMR spectroscopy.

The peptides of the invention, suitable formulated in administration forms together with acceptable excipients, may be used for treating NGF-related pathologies.

Examples of said pathologies include human corneal ulcer, pressure skin ulcers, chronic vasculitic ulcers in rheumatoid arthritis, cataract, dry eye syndrome, neuropahic pain, neuro-ectodermal tumor, neuroendocrine tumors, erectile dysfunction in diabetics, autoimmune encephalomyelitis, chronic constipation, peripheral neuropathy, genetic neuropathy, leprous neuropathy, diabetic neuropathy, cisplatin neuropathy, HIV-related neuropathy, Alzheimer's disease, Huntington's disease, multiple sclerosis, dementia, schizophrenia, depression, ischemic lesions, UV neurotoxicity, hair growth disturbances (alopecia, effluvium, hirsutism). The peptides will be administered parenterally, orally or topically at a dose which will be determined by the skilled practitioner according to the pathology and to the pharmaco-toxicological properties of the selected peptide.

The following examples will further describe the invention.

Example 1

Chemical Synthesis of Peptide L1L4

Figure 1:
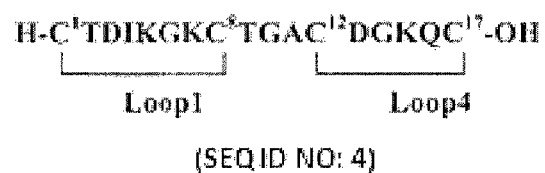
FIG. 1. Amino acid sequence of the peptides L1L4, AcL1L4 and AcNL1L4
Figure 1:
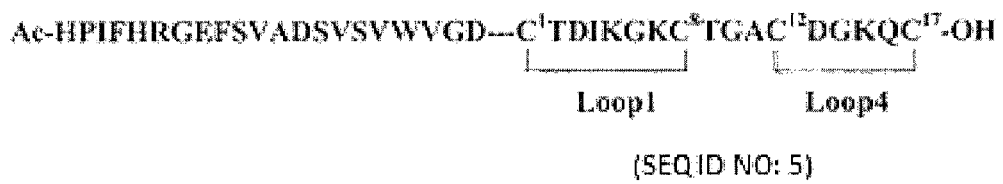

The peptide having the sequence as reported in FIG. 1, and named L1L4, was synthesized using Fmoc solid phase strategy followed by disulphide bridge formation in solution. The solid phase synthesis was performed to obtain the linear precursor of L1L4. The synthesis was carried out with Fmoc-Cys(Acm)-Wang resin (substitution 0.60 mmol g$^{-1}$) to reduce the racemization level due to the esterification of protected cysteine residue onto the resin. In order to obtain the selective formation of the two disulphide bridges ($Cys^1/Cys^8$ and $Cys^{12}/Cys^{17}$) S-Trt TFA-labile protecting group for $Cys^1$ and $Cys^8$ and S-Acm group for the remaining two Cys residues were used.

The deprotection step (removal of the Fmoc group) was performed with 30% piperidine in DMF and active ester coupling reactions were performed using HBTU (4 equivalents) as coupling reagent and DIEA (8 equivalents) in DMF. Each coupling was repeated twice and monitored by Kaiser test.

The peptide was cleaved off the resin and deprotected using a mixture of TFA/H$_2$O/Phenol/Thioanisole/EDT/TIS (81.5:5:5:5:2.5:1 v/v/v/v/v/v). The resin was then filtered off and L1L4 linear precursor was precipitated using ethyl ether.

The crude product containing his (thiol) and bis(Acm) cysteines was purified by preparative HPLC on the HP 1100 system equipped with a Diode Array HP 1100 using a Phenomenex $C_{18}$ column (4.6×250 mm; 5 µm; 300 A) and a linear gradient of $H_2O$ (0.1% TFA)/$CH_3CN$ (0.1% TFA) from 5% to 70% of $CH_3CN$ (0.1% TFA) in 35 min at flow rate of 20 ml/min. The purified peptide was characterized using matrix-assisted laser desorption ionization mass spectrometry (MALDI-MS) on a MALDI-TOF Voyager-DE (Perseptive Biosystem) spectrometer. The MALDI-tof analysis gave the molecular ion peak [M-H$^+$] of 1874 as expected for the linear precursor.

The first oxidation to obtain the disulphide bridge $Cys^1$-$Cys^8$ was carried out in the presence of atmospheric oxygen, at high diluition (0.1 mM) in phosphate buffer at pH 7-8 for 24 h. The reaction was monitored by HPLC.

The reaction to obtain the disulphide bridge $Cys^{12}$-$Cys^{17}$ was performed by iodine-mediated oxidation. The S-Acm deprotection/oxidation step was carried out at high diluition (0.1 mM) in Ac—OH/$H_2O$ (1:1) in the presence of iodine (10 equivalents) for 30 min.

The rate of the oxidation was followed by HPLC and the iodine excess was quenched by sodium thiosulphate.

The peptide containing the two disulphide bridges was purified by preparative HPLC in the same conditions used for the linear precursor (see above). The final product was identified by MALDI-Tof spectrometry which gave the expected molecular ion peak [M-H$^{-1}$] of 1730 Da.

Example 2

Chemical Synthesis of Peptides AcL1L4 and AcNL1L4

The peptide AcL1L4 was synthesized according to the above reported procedure for the non-acetylaed compound. At the end of the synthesis before the cleavage/deprotection step the peptide N-terminus was acetylated on the resin using $Ac_2O$/DIEA/DMF (2.6:4.8:92.6 v/v/v). The final product was identified by MALDI-Tof spectrometry which gave the expected molecular ion peak [M-H$^{-1}$] of 1772 Da.

The peptide AcNL1L4, whose sequence is reported in FIG. 1, was synthesized using Fmoc solid phase strategy followed by disulphide bridge formation in solution. The solid phase synthesis was performed to obtain the linear precursor of AcNL1L4. The synthesis was carried out with Fmoc-Cys (Acm)-Wang resin (substitution 0.60 mmol g$^{-1}$) to reduce the racemization level due to the esterification of protected cysteine residue onto the resin. In order to obtain the selective formation of the two disulphide bridges ($Cys^1$/$Cys^8$ and $Cys^{12}$/$Cys^{17}$) S-Trt TFA-labile protecting group for $Cys^1$ and $Cys^8$ and S-Acm group for the remaining two Cys were used.

The deprotection step (removal of the Fmoc group) was performed with 30% piperidine in DMF and active ester coupling reactions were performed using HBTU (4 equivalents) as coupling reagent and DIEA (8 equivalents) in DMF. Each coupling was repeated twice and monitored by Kaiser test. At the end of the synthesis before the cleavage/deprotection step the peptide N-terminus was acetylated on the resin using $Ac_2O$/DIEA/DMF (2.6:4.8:92.6 v/v/v).

The peptide was cleaved off the resin and deprotected using a mixture of TFA/$H_2O$/Phenol/Thioanisole/EDT/TIS (81.5:5:5:5:2.5:1 v/v/v/v/v/v). The resin was then filtered off and AcNL1L4 linear precursor was precipitated using ethyl ether.

The crude product containing his (thiol) and bis(Acm) cysteines was purified by preparative HPLC on the HP 1100 system equipped with a Diode Array HP 1100 using a Phenomenex $C_{18}$ column (4.6×250 mm; 5 µm; 300 A) and a linear gradient of $H_2O$ (0.1% TFA)/$CH_3CN$ (0.1% TFA) from 5% to 70% of $CH_3CN$ (0.1% TFA) in 35 min at flow rate of 20 ml/min. The purified peptide was characterized using matrix-assisted laser desorption ionization mass spectrometry (MALDI-MS) on a MALDI-TOF Voyager-DE (Perseptive Biosystem) spectrometer. The MALDI-tof analysis gave the molecular ion peak [M-H$^+$] of 4239 Da as expected for the linear precursor.

The first oxidation to obtain the disulphide bridge $Cys^1$-$Cys^8$ was carried out in the presence of atmospheric oxygen, at high diluition (0.1 mM) in phosphate buffer at pH 7-8 for 24 h. The reaction was monitored by HPLC.

The reaction to obtain the disulphide bridge $Cys^{12}$-$Cys^{17}$ was performed by iodine-mediated oxidation. The S-Acm deprotection/oxidation step was carried out at high diluition (0.1 mM) in Ac—OH/$H_2O$ (1:1) in the presence of iodine (10 equivalents) for 30 min.

The rate of the oxidation was followed by HPLC and the iodine excess was quenched by sodium thiosulphate.

The peptide containing the two disulphide bridges was purified by preparative HPLC in the same conditions see above for the linear precursor.

The final product was identified by MALDI-Tof spectrometry which gave the expected molecular ion peak [M-H$^+$] of 4093 Da.

Example 3

Determination of trkA Phosphorylation

The biological activity of the peptides of invention was determined by analyzing their ability to induce the phosphorylation of the high affinity receptor trkA. Immunoblot analysis of trkA phosphorylation in PC12 cells was carried out as previously described (Colangelo et al., 1994). PC12 cells were treated for 5 min with the culture medium alone, or containing the NGF peptides (1-50 µM), or 2.5 S NGF (from 0.096 to 0.384 nM), washed and lysed at 4° C. in 1 ml of RIPA buffer (50 mM Tris pH 7.5, 150 mM NaCl, 1% Nonidet P-40, 0.5% sodium deoxycholate, 0.1% SDS and 1 mM DTT) containing protease inhibitors (2 mM PMSF, 1 µg/ml leupeptin, 5 µg/ml aprotinin) and phosphatase inhibitors (10 mM NaF and 1 mM sodium orthovanadate). Lysates (300 µg of total proteins) were incubated overnight at 4° C. with 2 µg of rabbit anti pan-trk IgG (C-14, Santa Cruz Biotechnology, CA) followed by incubation with protein A-Sepharose (Sigma) for additional 2 hr at 4° C. Precipitates were washed four times with RIPA buffer and the immunocomplexes resuspended in sample buffer (50 mM Tris pH 6.8, 2% sodium dodecyl sulfate, 100 mM DTT, 10% glycerol, 0.1% bromophenol blue), separated on 7.5% SDS-PAGE and transferred to nitrocellulose. Blots were then probed overnight at 4° C. with either a mouse mAb p-trkA IgG1 (E-6, Santa Cruz Biotech., CA) or a mAb anti-phosphotyrosine (PY99, Santa Cruz Biotech., CA) in TBST, followed by incubation with HRP-conjugated donkey anti-mouse IgG (Jackson Immunoresearch; 1:10,000) for 1 hr at room temperature. Detection of phosphorylated-trkA was carried out by using the enhanced chemiluminescence system (ECL, Amersham Pharmacia Biotech), while quantitation of the p-trkA bands was performed by densitometric analysis of the bands by using the Scion Image software. The activity was evaluated as fold of induction versus control (untreated cells).

As shown in FIG. 3, our data indicate that the NGF peptide L1L4 3 and 6 µM induces trkA phosphorylation in the range of 50-65% of that induced by 0.192 nM 2.5 S mNGF. Similar results were obtained with the NGF peptides AcL1L4 and AcNL1L4. The levels of trkA activation measured were much higher that that induced by single loop1 and loop4 peptides (data not shown). In addition, phosphorylation was inhibited by a 10 min preincubation of PC12 cells with the tyrosine kinase inhibitor K-252a (100 nM) before addition of the peptide compounds and it was similar to that obtained with the 2.5 S NGF.

Example 4

Evaluation of Neurotrophic Activity on Dorsal Root Ganglia (DRG)

Figure 2:
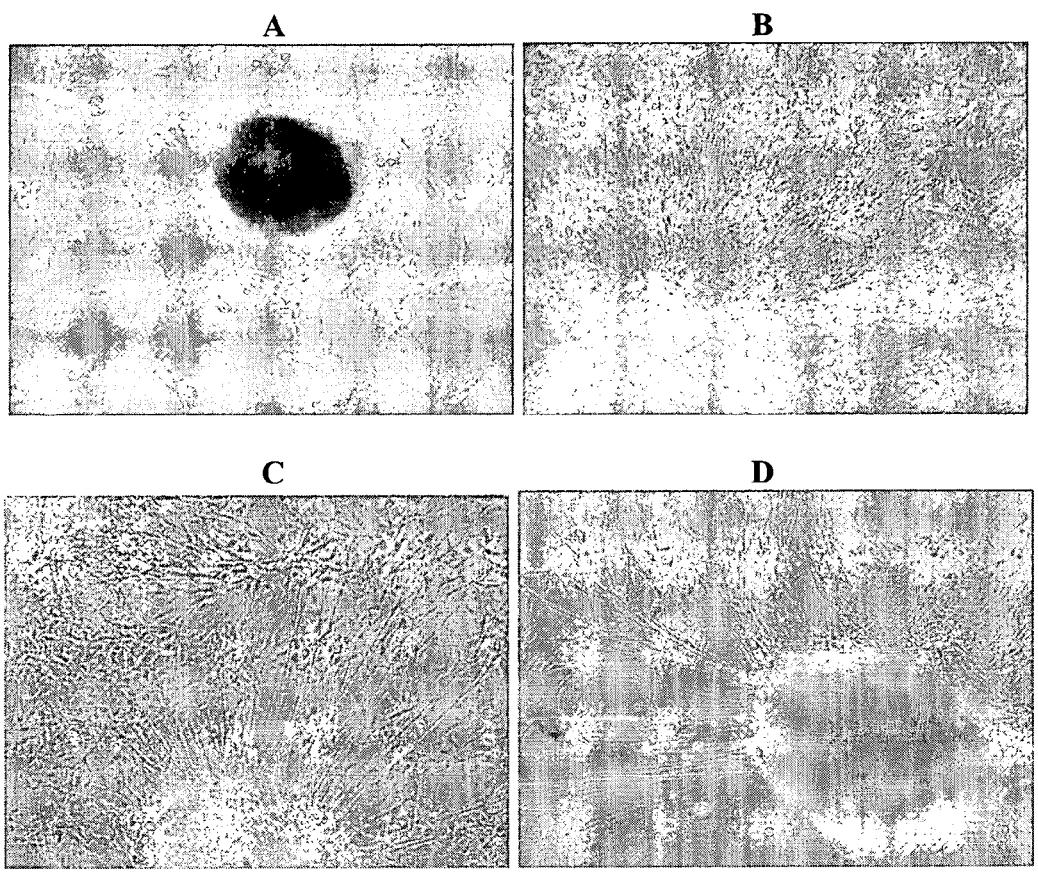
FIG. 2. Neurotrophic activity of NGF peptides L1L4 and AcL1L4

The biological activity of the peptides of the invention was also assessed by analyzing their ability to induce the differentiation and survival of dorsal root ganglia (DRG) (Levi-Montalcini, 1952). Explants of dorsal root ganglia (DRG) were prepared as previously described (Davies, 1989). Briefly, DRG were dissected from 8-days old chick embryos and immediately placed into Hepes Buffered Saline Solution (HBSS). Ganglia were then cultured onto poly-L-lysine (1%) precoated dishes in DMEM supplemented with 10% FBS, 2 mM L-glutamine, 100 µg/ml streptomycin, 100 U/ml penicillin. Treatments with NGF-mimetic peptides (2-50 µM) or 2.5 S mNGF (0.38 nM) were carried out immediately after plating and repeated every three days for about two-three weeks. As shown in FIG. 2, the NGF peptides L1L4 (C) and AcL1L4 (D) both at a concentration of 6 µM induced the differentiation of the DRG to an extent similar to that induced by 2.5 S mNGF (0.38 nM). The same level of DRG differentiation was induced by peptideconcentrations ranging between 3 and 20 µM. Notably, the peptides corresponding to either the single loop_1 or loop_4 do not show any detectable differentiation of the DRG when used at 6 µM.

The invention claimed is:

1. A peptide having a structure characterized by the presence of two loops constrained in cyclic structure by the presence of covalent bonds between amino acid side chains, the amino acid sequences of the first and the second loop being substantially homologous to that of loop 1 (residues 29-38) and of loop 4 (residues 92-97) of nerve growth factor (NGF), respectively, displaying NGF agonist or partial agonist activity.

2. A peptide according to claim 1 having the following formula:

(Xaa)n-AA1-(Yaa)m-AA2-L-AA3-(Zaa)m-AA4    (1)

wherein:
AA1 and AA2 are chosen from the group consisting of Cys, Asp, Glu, Lys, Orn, Pen, and Dap and are linked through an amide or S—S bond between chemical functions on their side chains;
AA3 and AA4 are chosen from the group consisting of Cys, Asp, Glu, Lys, Orn, Pen, and Dap and are linked through an amide or S—S bond between chemical functions on their side chains;
L is a linker sequence formed by 2-4 amino acid residues, an organic linker, or a mixed sequence of amino acid residues and organic linker;
(Yaa)m is an amino acid sequence formed by 4-8 residues;
(Zaa)m is an amino acid sequence formed by 4-8 residues;
(Xaa)n is an amino acid sequence in which n is an integer from 0 to 22.

3. A peptide according to claim 2 wherein L is the sequence TGA.

4. A peptide according to claim 2 wherein (Yaa)m is a sequence homologous to that of loop 1 (residues 29-38) of NGF.

5. A peptide according to claim 4 wherein the sequence (Yaa)m is TDIKGK (SEQ ID NO:1).

6. A peptide according to claim 2 wherein (Zaa)m is a sequence homologous to that of loop 4 (residues 92-97) of NGF.

7. A peptide according to claim 6 wherein the sequence (Zaa)m is DGKQ (SEQ ID NO:2).

8. A peptide according to claim 2 wherein (Xaa)n is a sequence homologous to that of the N-terminus of NGF.

9. A peptide according to claim 8 wherein the sequence (Xaa)n is HPIFHRGEFSVADSVSVWVGD (SEQ ID NO:3).

10. A pharmaceutical composition comprising a therapeutically effective amount of a peptide according to claim 1 and a pharmaceutically acceptable excipient.

11. A method for the treatment of an NGF-related pathology comprising administering the peptide of claim 1 to an individual in need of such treatment.

12. The method according to claim 11 wherein said pathology is selected from human corneal ulcer, pressure skin ulcers, chronic vasculitic ulcers in rheumatoid arthritis, cataract, dry eye syndrome, neuropathic pain, neuroectodermal tumor, neuroendocrine tumors, erectile dysfunction in diabetics, autoimmune encephalomyelitis, chronic constipation, peripheral neuropathy, genetic neuropathy, leprous neuropathy, diabetic neuropathy, cisplatin neuropathy, HIV-related neuropathy, Alzheimer's disease, Huntington's disease, multiple sclerosis, dementia, schizophrenia, depression, ischemic lesions, UV neurotoxicity, and hair growth.

13. A peptide according to claim 2, wherein (Yaa)m is a sequence homologous to that of loop 1 (residues 29-38) of NGF and (Zaa)m is a sequence homologous to that of loop 4 (residues 92-97) of NGF.

14. A peptide according to claim 13, wherein (Xaa)n is a sequence homologous to that of the N-terminus of NGF.

15. A peptide according to claim 13, wherein the sequence (Yaa)m is TDIKGK (SEQ ID NO:1) and the sequence (Zaa)m is DGKQ (SEQ ID NO:2).

16. A peptide according to claim 15, wherein the sequence (Xaa)n is HPIFHRGEFSVADSVSVWVGD (SEQ ID NO:3).

17. A peptide according to claim 2, wherein L is an organic linker.

18. A peptide according to claim 13, wherein L is an organic linker.

19. A peptide according to claim 14, wherein L is an organic linker.

20. A peptide according to claim 15, wherein L is an organic linker.

21. A peptide according to claim 16, wherein L is an organic linker.

* * * * *

UNITED STATES PATENT AND TRADEMARK OFFICE
CERTIFICATE OF CORRECTION

| | | |
|---|---|---|
| PATENT NO. | : 8,461,110 B2 | Page 1 of 1 |
| APPLICATION NO. | : 11/922043 | |
| DATED | : June 11, 2013 | |
| INVENTOR(S) | : Vitagliano et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1579 days.

Signed and Sealed this
Twenty-eighth Day of October, 2014

Michelle K. Lee
*Deputy Director of the United States Patent and Trademark Office*

SEQUENCE LISTING

```
<160> NUMBER OF SEQ ID NOS: 5

<210> SEQ ID NO 1
<211> LENGTH: 6
<212> TYPE: PRT
<213> ORGANISM: Unknown
<220> FEATURE:
<223> OTHER INFORMATION: artificial peptide having NGF agonist activity

<400> SEQUENCE: 1

Thr Asp Ile Lys Gly Lys
1               5

<210> SEQ ID NO 2
<211> LENGTH: 4
<212> TYPE: PRT
<213> ORGANISM: Unknown
<220> FEATURE:
<223> OTHER INFORMATION: artificial peptide having NGF agonist activity

<400> SEQUENCE: 2

Asp Gly Lys Gln
1

<210> SEQ ID NO 3
<211> LENGTH: 21
<212> TYPE: PRT
<213> ORGANISM: Unknown
<220> FEATURE:
<223> OTHER INFORMATION: artificial peptide having NGF agonist activity

<400> SEQUENCE: 3

His Pro Ile Phe His Arg Gly Glu Phe Ser Val Ala Asp Ser Val Ser
1               5                   10                  15

Val Trp Val Gly Asp
            20

<210> SEQ ID NO 4
<211> LENGTH: 17
<212> TYPE: PRT
<213> ORGANISM: Artificial Sequence
<220> FEATURE:
<223> OTHER INFORMATION: synthetic peptides
<220> FEATURE:
<221> NAME/KEY: DISULFID
<222> LOCATION: (1)...(8)
<220> FEATURE:
<221> NAME/KEY: DISULFID
```

-continued

```
<222> LOCATION: (12)...(17)

<400> SEQUENCE: 4

Cys Thr Asp Ile Lys Gly Lys Cys Thr Gly Ala Cys Asp Gly Lys Gln
1               5                   10                  15

Cys

<210> SEQ ID NO 5
<211> LENGTH: 38
<212> TYPE: PRT
<213> ORGANISM: Artificial Sequence
<220> FEATURE:
<223> OTHER INFORMATION: synthetic peptides
<220> FEATURE:
<221> NAME/KEY: ACETYLATION
<222> LOCATION: 1
<223> OTHER INFORMATION: N-terminal or other
<220> FEATURE:
<221> NAME/KEY: DISULFID
<222> LOCATION: (22)...(29)
<220> FEATURE:
<221> NAME/KEY: DISULFID
<222> LOCATION: (33)...(38)

<400> SEQUENCE: 5

His Pro Ile Phe His Arg Gly Glu Phe Ser Val Ala Asp Ser Val Ser
1               5                   10                  15

Val Trp Val Gly Asp Cys Thr Asp Ile Lys Gly Lys Cys Thr Gly Ala
                20                  25                  30

Cys Asp Gly Lys Gln Cys
                35
```